United States Patent
Cha

(10) Patent No.: US 7,625,702 B2
(45) Date of Patent: Dec. 1, 2009

(54) HELICAL WRAPPING OF SINGLE-WALLED CARBON NANOTUBES BY GENOMIC DNA

(75) Inventor: Jennifer Nam Cha, Union City, CA (US)

(73) Assignee: International Business Machines Corporation, Armonk, NY (US)

( * ) Notice: Subject to any disclaimer, the term of this patent is extended or adjusted under 35 U.S.C. 154(b) by 325 days.

(21) Appl. No.: 11/313,098

(22) Filed: Dec. 20, 2005

(65) Prior Publication Data
US 2007/0154891 A1 Jul. 5, 2007

(51) Int. Cl.
C12Q 1/68 (2006.01)
C12Q 1/70 (2006.01)
C12P 19/34 (2006.01)
C12M 1/00 (2006.01)
C07H 21/02 (2006.01)

(52) U.S. Cl. .............. 435/6; 435/5; 435/91.2; 435/283.1; 536/23.1; 977/734; 977/742; 977/746

(58) Field of Classification Search .......... 435/5, 435/6, 91.2, 283.1; 536/23.1; 977/734, 742, 977/746
See application file for complete search history.

(56) References Cited

U.S. PATENT DOCUMENTS

| | | | |
|---|---|---|---|
| 5,830,655 A * | 11/1998 | Monforte et al. ............ 435/6 |
| 6,656,693 B2 | 12/2003 | Saraf et al. | |
| 7,498,423 B2 * | 3/2009 | Zheng et al. ............ 536/23.1 |
| 2002/0172963 A1 | 11/2002 | Kelley et al. | |
| 2003/0134267 A1 | 7/2003 | Kang et al. | |
| 2004/0063100 A1 | 4/2004 | Wang | |
| 2004/0126802 A1 | 7/2004 | Brubaker | |
| 2004/0132072 A1 * | 7/2004 | Zheng et al. ............ 435/6 |
| 2004/0248144 A1 | 12/2004 | Mir | |
| 2005/0009039 A1 | 1/2005 | Jagota et al. | |

OTHER PUBLICATIONS

Dwyer et al, DNA functionalized single-walled carbon nanotubes, 2002, Nanotechnology, 13, 601-604.*
Barhoumi, Semi-Biosynthesis of DNA nanostructures, Marshall University thesis, May 2004, 1-123.*
Xin et al, DNA templated nanotube localization, 2003, JACS, 125, 8710-8711.*
Zheng, et al, Structure based carbon nanotube sorting by sequence dependent DNA assembly, 2003, Science, 302, 1545-1548.*
Nakashima et al, DNA dissolves single walled carbon nanotubes in water, 2003, Chemistry Letters, 32, 456-457.*
Katz, et al.; Biomolecule-functionalized carbon nanotubes: applications in nanobioelectronics; Institute of Chemistry, The Hebrew University of Jerusalem, Jerusalem, Israel; Chemphyschem. Aug. 20, 2004; 5(8):1084-104.
Bae, et al.; Electrochemical fabrication of single-walled carbon nanotubes-DNA complexes by poly(ethylenedioxythiophene) and photocurrent generation by excitation of an intercalated chromophore; Department of Chemistry and Biochemistry, Graduate School of Engineering, Kyushu University, Fukuoka 812-8581, Japan; Org Biomol Chem. Apr. 21, 2004; 2(8):1139-44. Epub Mar. 18, 2004.

(Continued)

Primary Examiner—J D Schultz
Assistant Examiner—Narayan K Bhat
(74) Attorney, Agent, or Firm—Schmeiser, Olsen & Watts

(57) ABSTRACT

A structure and method for forming single-stranded DNA segments/single-wall carbon nanotube complexes and a method of preparing single-stranded DNA segments. The method for forming single-stranded DNA segments/single-wall carbon nanotube complexes including: attaching single-stranded DNA segments to single-wall carbon nanotubes to form single-stranded DNA segment/single-wall carbon nanotube complexes, each of the single-stranded DNA segments having a same length of greater than 2,000 bases.

14 Claims, 5 Drawing Sheets

OTHER PUBLICATIONS

Keren, et al.; DNA-Templated Carbon Nanotube Field-Effect Transistor; Science, vol. 302; Nov. 21, 2003; pp. 1380-1381; www.sciencemag.org.

Lay, et al.; Simple Route to Large-Scale Ordered Arrays of Liquid-Deposited Carbon Nanotubes; 2004 American Chemical Society; Nano Letters 2004, vol. 4, No. 4; pp. 603-606; Published on Web Mar. 13, 2004.

Miller, et al.; Large-scale assembly of carbon nanotubes; 2003 Nature Publishing Group, vol. 425; Sep. 4, 2003; pp. 36-37; www.nature.com/nature.

Zheng, et al.; DNA-assisted dispersion and separation of carbon nanotubes; 2003 Nature Publishing Group, vol. 2; May 2003; pp. 338-342; www.nature.com/naturematerials.

Zheng, et al.; Structure-Based Carbon Nanotube Sorting by Sequence-Dependent DNA Assembly; Science, vol. 302; Nov. 28, 2003; pp. 1545-1548; www.sciencemag.org.

* cited by examiner

SEQUENCE LISTING

```
<160> NUMBER OF SEQ ID NOS: 2

<210> SEQ ID NO 1
<211> LENGTH: 50
<212> TYPE: DNA
<213> ORGANISM: Unknown
<220> FEATURE:
<223> OTHER INFORMATION: Suspected Synthetic, Purchased from Integrated
      DNA Technologies, Coralville,IA, USA

<400> SEQUENCE: 1
tgcagatact   cacctgcatc   ctgaacccat   tgacctccaa   ccccgtaata           50

<210> SEQ ID NO 2
<211> LENGTH: 50
<212> TYPE: DNA
<213> ORGANISM: Unknown
<220> FEATURE:
<223> OTHER INFORMATION: Suspected Synthetic, Purchased from Integrated
      DNA Technologies, Coralville, IA, USA

<400> SEQUENCE: 2
tggtgttgtg   tgtgagttcg   actggaatga   tggaaatggt   caggaaggat           50
```

HELICAL WRAPPING OF SINGLE-WALLED CARBON NANOTUBES BY GENOMIC DNA

FIELD OF THE INVENTION

The present invention relates to the field of forming carbon nanotube/DNA complexes. More specifically, the present invention relates to a method of forming single-stranded DNA molecules suitable for dispersing single-wall carbon nanotubes, a method of forming a single-wall carbon nanotube/single-stranded DNA complex, and a structure of a single-wall carbon nanotube/single-stranded DNA complex.

BACKGROUND OF THE INVENTION

Due to their nanometer sizes and molecular recognition capabilities, biological systems have garnered much attention as vehicles for the directed assembly of nanoscale materials. One of the largest challenges of this research has been to successfully interface biological systems with nanoscale materials, such as carbon nanotubes. To this end methods utilizing short DNA oligomers that can disperse single-wall carbon nanotubes in water have been developed. However, the need for specific repeating base sequences limits use of this method. Therefore, there is a need for DNA based methods to disperse single-wall carbon nanotubes without the limitations of specific repeating base sequences.

SUMMARY OF THE INVENTION

A first aspect of the present invention is a method, comprising: attaching single-stranded DNA segments to single-wall carbon nanotubes to form single-stranded DNA segment/single-wall carbon nanotube complexes, each of the single-stranded DNA segments having a length of greater than 2,000 bases.

A second aspect of the present invention is a method, comprising: replicating double-stranded DNA segments in a polymerase chain reaction in the presence of a first primer and a second primer, the second primer having a terminating thiol group attached to one end of the second primer, each replicated double-stranded DNA segment having first and second complementary strands, the second strand having a thiol group at one end of the second strand; attaching metal nanoparticles to the thiol groups of the replicated double-stranded DNA segments; breaking the replicated double-stranded DNA segments into complementary first and second single-stranded DNA segments, the second single-stranded DNA segments including the thiol groups and metal nanoparticles; and removing the first single-stranded DNA segments from the second single-stranded DNA segments.

A third aspect of the present invention is a structure, comprising: a single-wall carbon nanotube; and a single-stranded DNA segment helically wound around the single-wall carbon nanotube, the single-stranded DNA segment being greater than 2,000 bases in length.

BRIEF DESCRIPTION OF DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

Carbon nanotubes (CNTs) are closed-cage molecules composed of $sp^2$-hybridized carbon atoms arranged in hexagons and pentagons. Carbon nanotubes may be single-wall nanotubes (SWNT) which are hollow tube like structures or multi-walled nanotubes (MWNT) which resemble sets of concentric cylinders. For the purposes of the present invention, the terms carbon nanotube (CNT) and is single-wall nanotube (SWNT) are defined single-wall carbon nanotubes. The SWNTs of the present invention may be doped with elements other than carbon, examples of which include, but are not limited to phosphorus, arsenic, boron and metals.

SWNTs may be made by any number of methods known in the art and are commercially available. In one example, SWNTs are made using high pressure carbon monoxide process (HiPCo) process (P. Nikolaev et al. *Chem Phys. Lett.* 313, 91-97 (1999)).

In the interest of using DNA as a dispersion and patterning vehicle for SWNTs for use in microelectronics, the ideal linearly extended length of the DNA should be in the order of several microns. DNA length may also be expressed as the number of base pairs (bp) attached to the phosphate backbone of the DNA molecule. The DNA utilized by the present invention is genomic DNA. Though coliphage lambda DNA was used in the experimental portions of the present invention, the invention is not limited to being practiced with lambda DNA and any genomic DNA may be used. Lambda DNA was chosen because its entire 48,502 base pair sequence is known and its restriction enzyme map fully characterized. Lambda DNA is derived from *E. coli* and is commercially available.

Figure 1:
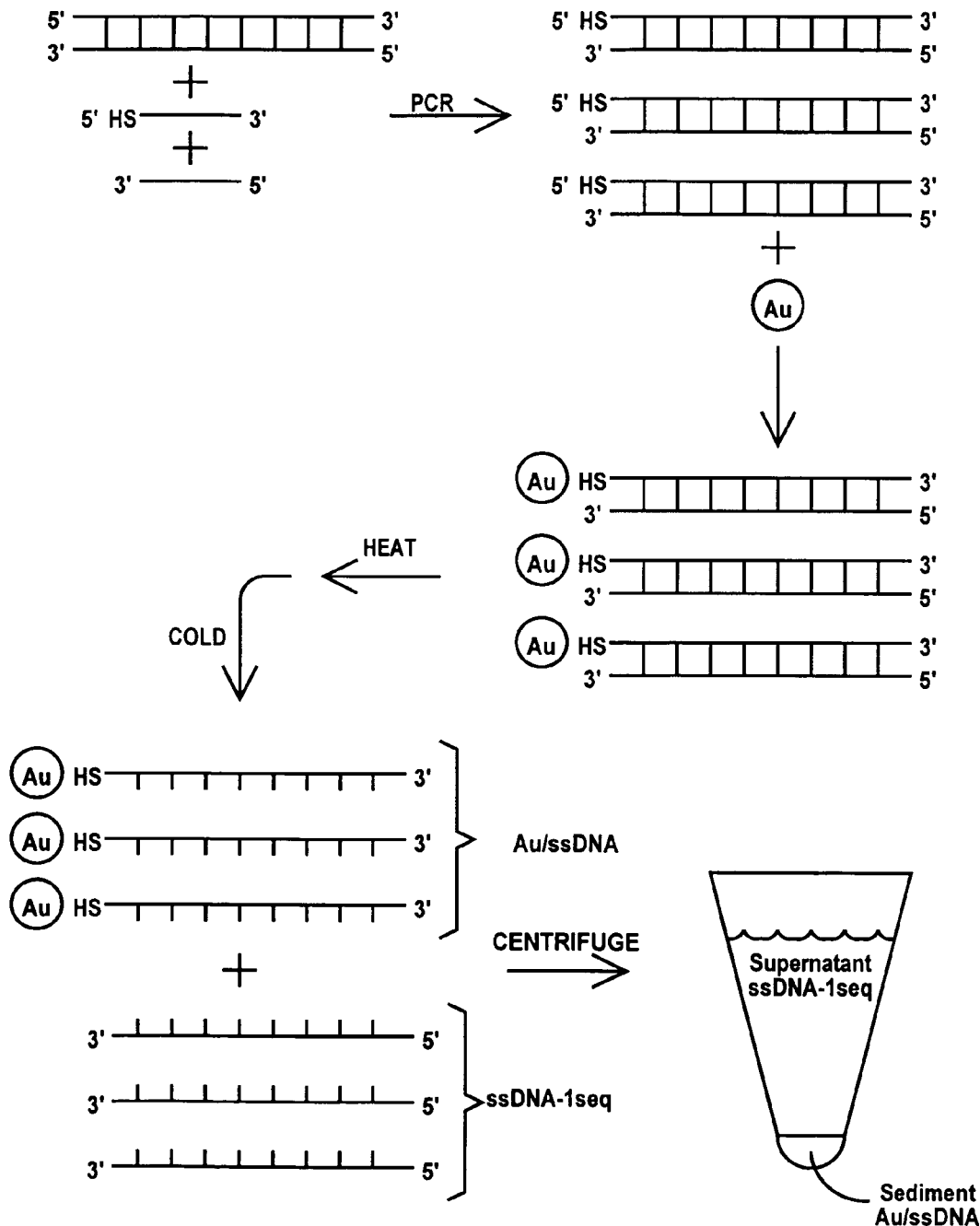
FIG. 1 is a schematic representation of the preparation of single-stranded DNA and single-wall CNT/single-stranded DNA complexes according to embodiments of the present invention.

FIG. 1 is a schematic representation of the preparation of single-stranded DNA and single-wall CNT/single-stranded DNA complexes according to embodiments of the present invention. In FIG. 1, the first step is to perform a polymerase chain reaction (PCR) designed to amplify a long length base pair segment of double-stranded DNA (dsDNA) (the template dsDNA) using two short base pair length primers. One of the primers is modified to include a thiol (—SH) group on its 5' end. The other primer is unmodified. The dsDNA may be prepared by digestion of a longer dsDNA using a restriction enzyme. The amplified dsDNA segments (now thiolated dsDNA) are modified from the original dsDNA segment by having thiol groups on the 5' end of one strand of the dsDNA segments.

In FIG. 1, the second step is to mix the thiolated dsDNA prepared in step 1, with phosphine-capped Au nanoparticles (about 5 to 25 nm in diameter) using an about 0.5 to about 1 molar ratio of thiolated dsDNA to Au. This binds a Au nanoparticle to the thiol groups of the thiolated dsDNA to produce Au/thiolated dsDNA complex (Au/dsDNA). The resultant mixture is centrifuged to separate the Au/dsDNA from unbound dsDNA.

In FIG. 1, the third step is to denature the Au/dsDNA into Au/thiolated ssDNA complex (Au/ssDNA) and free single-stranded DNA (ssDNA-1seq). In one example, denaturing is accomplished by heating and then quickly cooling the Au/dsDNA.

In FIG. 1, the fourth step is to centrifuge the Au/ssDNA and ssDNA-1seq mixture to collect the Au/ssDNA in the sediment leaving the ssDNA-1seq in the supernatant. The supernatant can then be decanted off and lyophilized to dryness. The Au/ssDNA may later be reconstituted by mixing with water to any concentration desired. The reconstituted ssDNA-1seq solution or, alternatively, the supernatant itself may be mixed with SWNTs as described infra. The ssDNA-1seq cannot self-hybridize through complementary base pairing. The length of dsDNA and the length of ssDNA-1seq is the same. In one example, the ssDNA-1seq has an extended length of about 1.4 microns. In another example, the length the ssDNA-1seq is greater than 2,000 bp. In still another example, the length the ssDNA-1seq is between about 3,000 bp and about 50,000 bp. In another example, the ssDNA-1seq has a linearly extended length greater than 1 micron.

To form single-stranded DNA segment/single-wall carbon nanotube complexes (ssDNA/SWNT), ssDNA-1seq solutions are mixed with SWNTs and sonicated (energy supplied by sound waves) at low temperatures to prevent overheating (in one example, about 4° C.) which are kept in solution by the ssNDA-1seq while un-complexed SWNT will not remain suspended and can be removed by centrifuging. In one example, about 90% of the SWNTs are complexed.

Atomic force microscopy (AFM) indicates the ssDNA/SWNT complex comprises an ssDNA strand helically wound around a SWNT. In one example, the ssDNA wrapped SWNTs had diameters between about 0.5 nanometer and about 2.0 nanometers and lengths between about 0.7 microns and about 2.0 microns. Atomic force microscopy (AFM) also indicates that on any particular SWNT the pitch of the ssDNA wrapping is constant, in one example about 60 nm, but from SWNT to SWNT the pitch could vary. In one example the pitch of the ssDNA wrapping on any particular SWNT is a constant between about 12 nm and about 80 nm.

Applicants have found that when a dsDNA segment is used to generate a ssDNA-1 seq using the methods described supra and an identical dsDNA segment is used to generate an ssDNA-2seq (by conventional denaturing methods) having complementary ssDNA strands, the ssDNA-2seq will not complex SWNTs. See FIG. 3A and description infra. Further, the random sequence of bases (random because it was genomic) of the dsDNA used is in direct contradiction to current theories that an ssDNA with non-random base sequences is required to complex SWNTs, that ssDNA complexing of SWNTs involves reconciliation of specific CNT structures, that ssDNA complexing of SWNTs occurs only with ssDNA having lengths under 2,000 bp or that the tight helix formation around CNTs is ssDNA base pair sequence dependent.

Figure 3A:
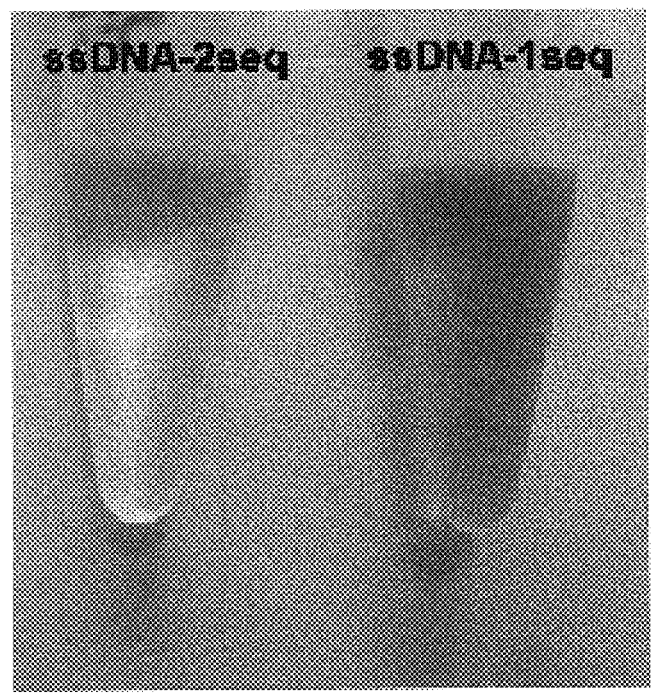
FIG. 3A is a photographic comparison of single-stranded DNA-1seq mixed with single-wall carbon nanotubes and complementary single-stranded DNA-2seq mixed with SWNTs.

FIG. 3A is a photographic comparison of ssDNA-1seq mixed with SWNTs and complementary ssDNA-2seq mixed with SWNTs. The tube labeled ssDNA-seq2 is clear indicating no reaction of ssDNA-seq2 with the SWNTs, while the tube labeled ssDNA-seq1 is dark indicating binding of ssDNA-seq1 with the SWNTs.

High density arrays of ssDNA/SWNT can be produced by air-drying droplets of ssDNA/SWNT solution on aminopropyltriethoxysilane (APTES) terminated silicon substrates which would be useful in microelectronic or nanoelectronic applications.

EXPERIMENTAL

Materials (1) Lambda DNA was purchased from Invitrogen, Carlsbad, Calif.

(2) NdeI enzyme was purchased from New England Biolabs, Ipswich, Mass.

(3) All DNA primers were purchased from Integrated DNA Technologies, Coralville, Iowa.

(4) HiPCo carbon nanotubes were purchased from Carbon Nanotechnologies.

(5) (bis)p-sulfonatophenyl)phenylphosphine dihydrate, dipotassium salt was purchased from Strem Chemical, Newburyport, Mass.

(6) Sodium citrate capped Au nanoparticles were purchased from Ted Pella, Redding, Calif.

(7) Phosphine capped Au nanoparticles were prepared by "ligand exchange" by mixing 30 mg of (bis)p-sulfonatophenyl)phenylphosphine dihydrate, dipotassium salt with a 100 ml suspension of sodium citrate capped Au nanoparticles and stirring overnight. Phosphine capped Au nanoparticles were collected by adding sodium chloride to the suspension to precipitate the phosphine capped Au nanoparticles. The phosphine capped Au nanoparticles were then re-suspended in deionized water.

Preparation of 5' Thiolated dsDNA

Template dsDNA was prepared by digesting lambda DNA with the restriction enzyme NdeI and collecting the 3796 bp lambda DNA segments. To 1 µg /100 µl PCR reactants of the 3796 bp lambda DNA segments 100 nM of a first (thiolated) primer having the sequence (SEQ ID NO: 1): 5'-SH-TGCA-GATACTCACCTGCATCCTGAACCCAT-TGACCTCCAACCCCGTAATA-3'. and 100 nM of a second (non-thiolated) primer having the sequence (SEQ ID NO: 2): 5'-TGGTGTTGTGTGTGAGTTCGACTGGAAT-GATGGAAATGGTCAGGAAGGAT-3'. 100 nM were added. Touchdown PCR was performed with 40 cycles at 95° for 30 seconds, 60° C. for 45 seconds and 72° C. for 5 minutes to generate thiolated lambda DNA having a length of 3796 bp.

Figure 2A:
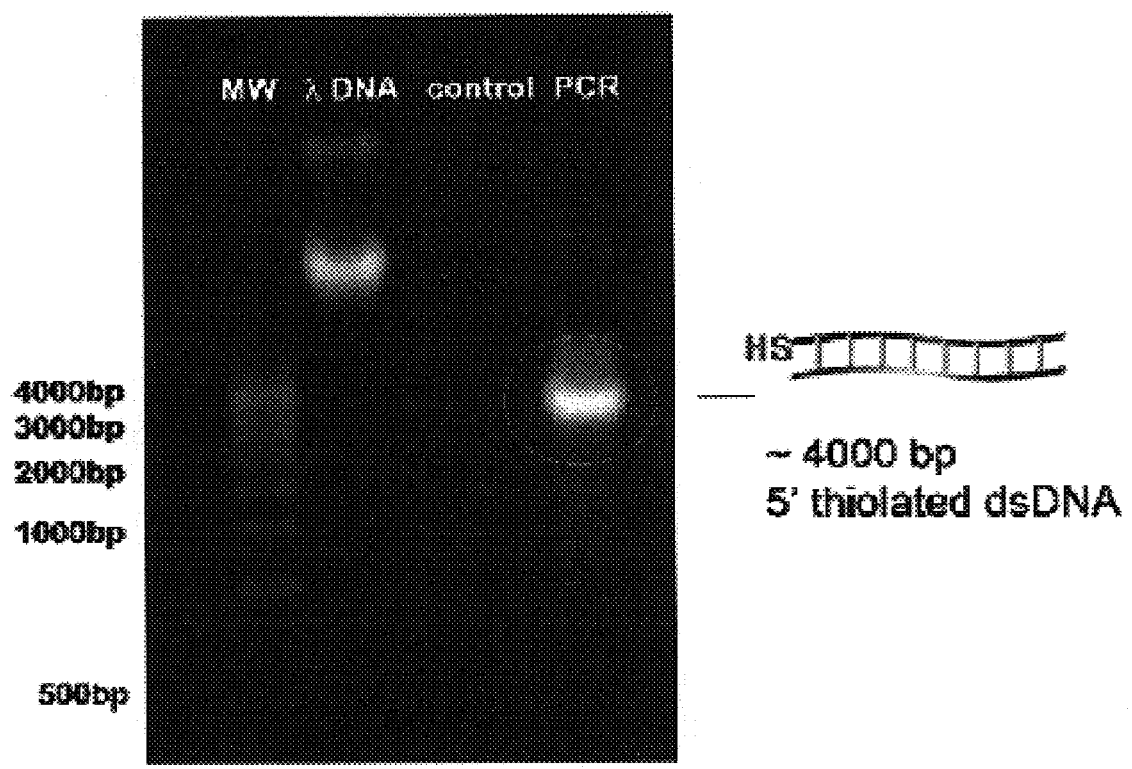
FIG. 2A is a photograph of a gel electrophoresis analysis of a thiolated lambda DNA polymerase chain reaction amplification procedure before centrifuging.

FIG. 2A is a photograph of a gel electrophoresis analysis of the thiolated lambda DNA PCR amplification procedure just described. In FIG. 2A, the column labeled "MW" includes molecular weight markers; the column labeled "λDNA" includes starting lambda DNA only; the column labeled "control" includes the products of a PCR using primer 1 and primer 2 only, and the column labeled "PCR" includes the result of the primers and lambda DNA PCR reaction.

Preparation of Au/dsDNA Complex

Figure 2B:
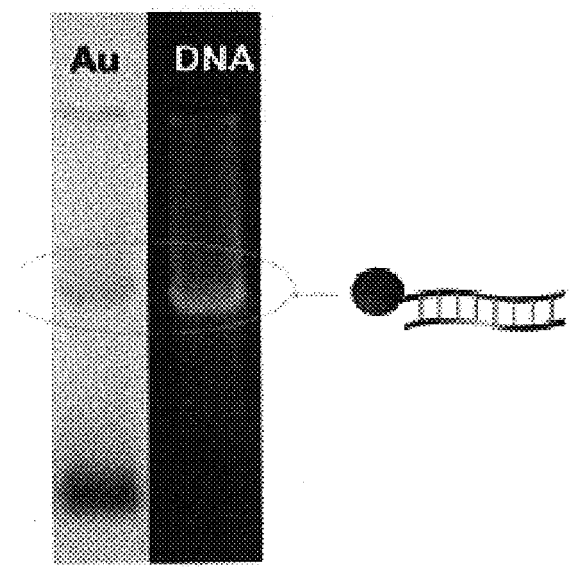
FIG. 2B is photograph of a gel electrophoresis analysis of a gold/double-stranded DNA preparation procedure.

The thiolated lambda dsDNA prepared supra, was mixed with phosphine-capped 15 nm gold particles using several different 0.5 to 1 molar ratios of thiolated dsDNA to Au nanoparticles. Typically, after 1 hour, the mixture was centrifuged, unbound thiolated dsDNA collected in the supernatant and Au/thiolated dsDNA complex (Au/dsDNA) collected in the sediment FIG. 2B is photograph of a gel electrophoresis analysis of the Au/dsDNA preparation procedure just described before centrifuging. In FIG. 2B, under white light (on the left), Au nanoparticles are seen while under UV light (on the right) ethidium bromide (EtBr) stained Au/dsDNA is seen. A Au band and the Au/dsDNA band (circled) are detected at the same distance, indicating binding of Au nanoparticles to thiolated dsDNA.

Figure 2C:
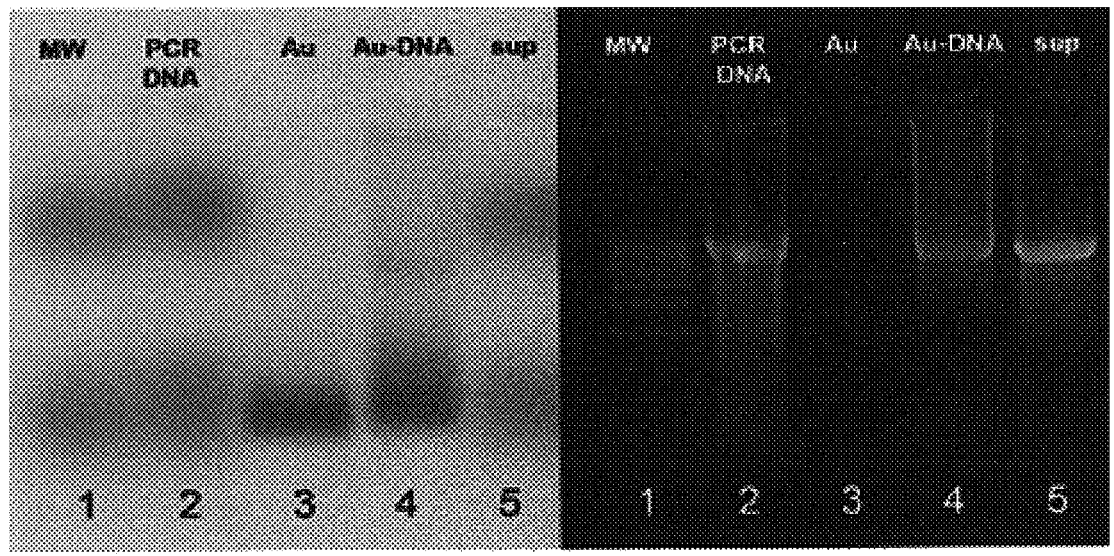
FIG. 2C is photograph of a gel electrophoresis analysis of the gold/double-stranded DNA preparation procedure after centrifuging.

FIG. 2C is photograph of a gel electrophoresis analysis of the Au/dsDNA preparation procedure just described after centrifuging. In FIG. 2C, on the left, lanes 1 through 5 are viewed under white light and on the right, lanes 1 through 5 are viewed under UV light. Lane 1 includes molecular weight markers. Lane 2 includes the 5' thiolated dsDNA which preparation was described supra. Lane 3 includes only 15 nm gold nanoparticles. Lane 4 includes re-suspended sediment containing the Au/ssDNA. Lane 5 includes the supernatant obtained after centrifugation. As is observed in lanes 4 and 5, while some of the thiolated dsDNA did indeed bind to the gold nanoparticles, a small portion of the dsDNA did not bind the gold nanoparticles.

Preparation of ssDNA

A dispersion of Au/dsDNA (from the sediment described supra in the preparation of Au/dsDNA) was thermally denatured at 98° C. and quenched on ice to produce a mixture of Au/ssDNA complex (Au/ssDNA) and unbound ssDNA. This mixture was centrifuged and the supernatant containing unbound ssDNA recovered.

ssDNA Dispersion of Carbon Nanotubes

Less than 1 mg of HiPCo nanotubes were added to 10 μg/ml solutions of the unbound ssDNA and sonicated in an ice-water bath for 10 to 20 minutes. Any insoluble material was removed after centrifugation at speeds of 400 to 1000 rpm. 10 μl droplets of ssDNA or ssDNA/SWNT solutions containing 50 mM of $MgCl_2$ were deposited on freshly cleaved mica surfaces, air dried, rinsed with water and dried under argon prior to imaging. 10 μl droplets were also deposited and dried on aminoproyltrethoxysilane (APTES) treated Si wafers but with no addition of $MgCl_2$. The APTES was deposited in a silylation oven purchased from Yield Engineering Systems, San Jose, Calif. at 150° C. for 30 minutes. All imaging was done in tapping mode in air.

Figure 3B:
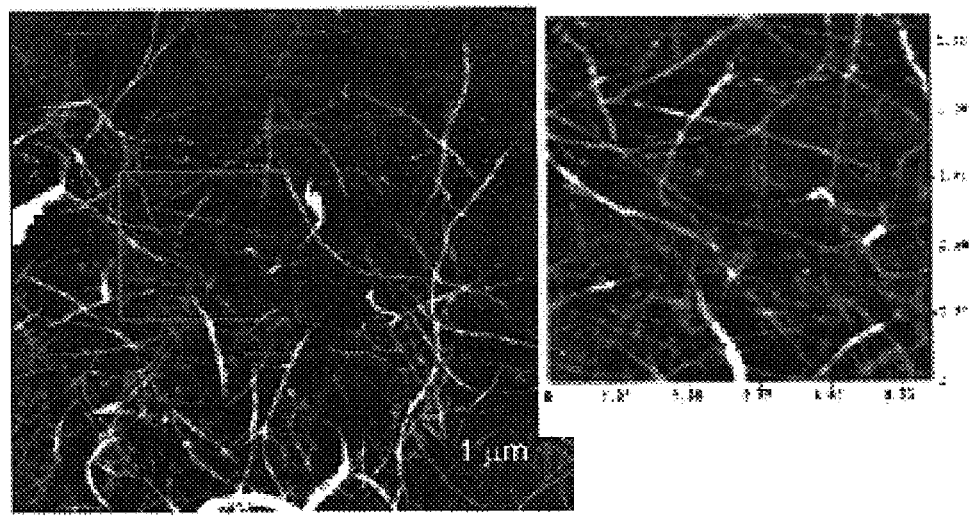
FIG. 3B is a photograph of a low magnification atomic force microscope scan of single-wall nanotube/single strand DNA complexes bound to mica.

FIG. 3B is a photograph of a low magnification atomic force microscope scan of ssDNA/SWNT prepared bound to mica. In FIG. 3B, the photograph on the left is a large area height AFM scan of ssDNA bound to SWCTs on mica. The photograph on the right is a close-up of large area scan on the left.

Figure 3C:
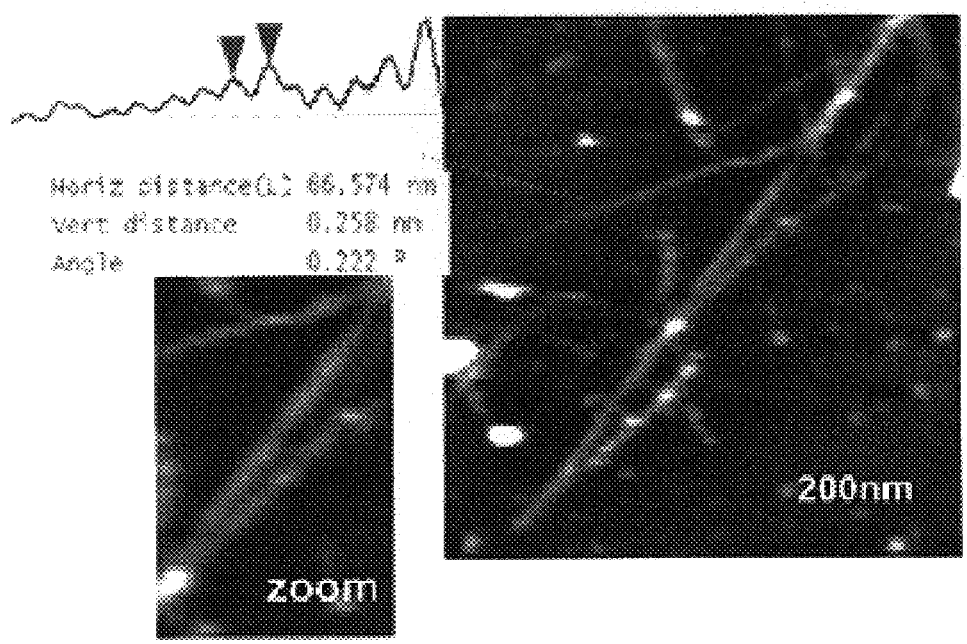
FIGS. 3C, 3D and 3E are photographs of high magnification atomic force microscope scans of single-wall nanotube/single strand DNA complexes bound to mica.
Figure 3D:
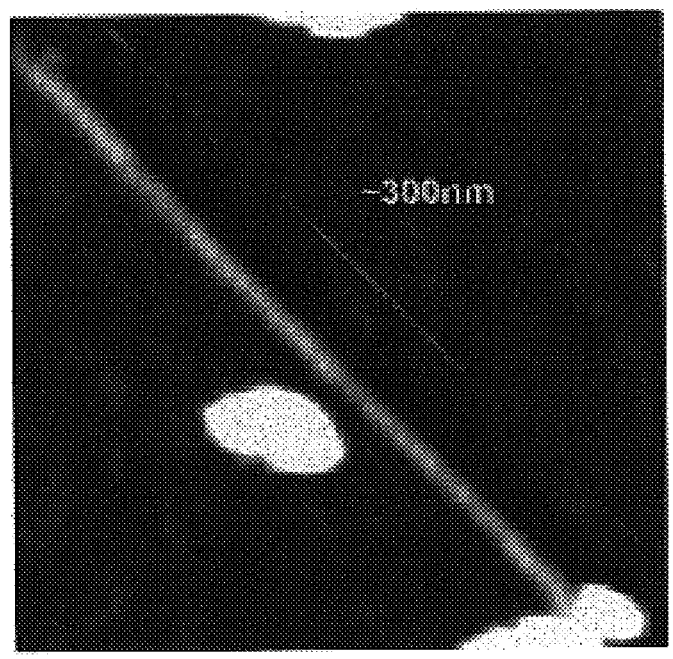
Figure 3E:
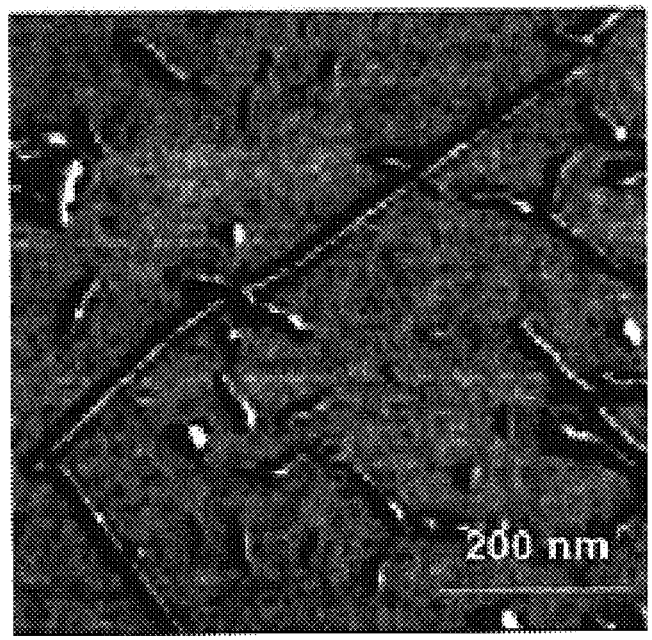

FIGS. 3C, 3D and 3E are photographs of high magnification atomic force microscope scans of ssDNA/SWNT complexes bound to mica. In FIG. 3C, on the right is a low magnification image of ssDNA/SWNTs. On the left is a height AFM image of one particular ssDNA/SWNT and above the left image is a section analysis of the one particular ssDNA/SWNT indicated by the arrows. Section analysis gives a ssDNA wrapping pitch of about 60 nm for that one particular ssDNA/SWNT. The difference in pitch should be noted in the particular structure shown in the center of the right hand image and in the left hand zoomed image. In FIG. 3D, a single ssDNA/SWNT is shown and the helically wrapping is clearly shown. In FIG. 3E, several ssDNA/SWNTs are shown. Again the helical wrapping is clearly shown.

Thus, the present invention provides DNA based methods to disperse single-wall carbon nanotubes without the limitations of specific repeating base sequences.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore, it is intended that the following claims cover all such modifications and changes as fall within the true spirit and scope of the invention.

What is claimed is:

1. A method, comprising:
helically wrapping single-stranded lambda DNA segments around a single-wall carbon nanotube to form single-stranded DNA segment/single-wall carbon nanotube complex, each single-stranded DNA segment of said single-stranded DNA segments having a length of between about 3,000 and about 50,000 bases.

2. The method of claim 1, wherein said single-stranded DNA segments are base sequences of naturally occurring DNA molecules.

3. The method of claim 1, wherein said single-stranded DNA segments are base sequences of bacteriophage lambda DNA.

4. The method of claim 1, wherein said single-stranded DNA segments would have lengths greater than 1 micron if they were linearly extended.

5. The method of claim 1, wherein each of said single-stranded DNA segments has an identical random base sequence.

6. The method of claim 1, wherein each of said single-stranded DNA segments has an identical base length.

7. The method of claim 1, wherein individual single-stranded DNA segments are helically wrapped around respective single-wall carbon nanotubes.

8. The method of claim 1, wherein said single-wall carbon nanotubes have a diameter of between about 0.5 nanometer and about 2.0 nanometers and have a length between about 0.7 microns and about 2.0 microns.

9. The method of claim 1, including:
mixing said single-wall carbon nanotubes and said single-stranded DNA segments in water and sonicating the resultant mixture.

10. The method of claim 1, further including:
binding said single-stranded DNA segment/single-wall carbon nanotube complexes to a substrate.

11. The method of claim 10, wherein said single-wall carbon nanotube and said single stranded DNA segments of said single-stranded DNA segment/single-wall carbon nanotube complex are orientated in a substantially same direction relative to a top surface of said substrate.

12. The method of claim 1, further including:
replicating double-stranded DNA segments in a polymerase chain reaction in the presence of a first primer and a second primer, said second primer having a terminating thiol group attached to one end of said second primer, each replicated double-stranded DNA segment having first and second complementary strands, said second strand having a thiol group at one end of said second strand;
attaching metal nanoparticles to said thiol groups of said replicated double-stranded DNA segments;
breaking said replicated double-stranded DNA segments into complementary first and second single-stranded DNA segments, said second single-stranded DNA segments including said thiol groups and metal nanoparticles; and
removing said first single-stranded DNA segments from said second single-stranded DNA segments.

13. The method of claim 12, wherein said metal nanoparticles are phosphine-capped gold nanoparticles and said removing said first single-stranded DNA segments from said second single-stranded DNA segments includes centrifuging a suspension of said first single-stranded DNA segments and said second single-stranded DNA segments in water to form a supernatant and a sediment, wherein second single-stranded DNA segments are in said sediment and first single-stranded DNA segments are in said supernatant.

14. The method of claim, 13, further including:
removing said supernatant from said sediment; and
mixing single-wall carbon nanotubes with said removed supernatant to form single-stranded DNA segment/single-wall carbon nanotube complexes.

* * * * *

UNITED STATES PATENT AND TRADEMARK OFFICE
CERTIFICATE OF CORRECTION

PATENT NO. : 7,625,702 B2
APPLICATION NO. : 11/313098
DATED : December 1, 2009
INVENTOR(S) : Jennifer Nam Cha It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this

Second Day of November, 2010

David J. Kappos
*Director of the United States Patent and Trademark Office*